United States Patent
Shimatani et al.

(10) Patent No.: US 9,463,165 B2
(45) Date of Patent: Oct. 11, 2016

(54) GRANULAR MATERIAL FOR ORALLY FAST DISINTEGRATING TABLETS

(71) Applicant: TEIKA PHARMACEUTICAL CO., LTD., Toyama (JP)

(72) Inventors: Takao Shimatani, Toyama (JP); Takahiro Kawagishi, Toyama (JP)

(73) Assignee: TEIKA PHARMACEUTICAL CO., LTD., Toyama (JP)

( * ) Notice: Subject to any disclaimer, the term of this patent is extended or adjusted under 35 U.S.C. 154(b) by 0 days.

(21) Appl. No.: 14/423,446

(22) PCT Filed: Sep. 4, 2013

(86) PCT No.: PCT/JP2013/073808
§ 371 (c)(1),
(2) Date: Feb. 24, 2015

(87) PCT Pub. No.: WO2014/038593
PCT Pub. Date: Mar. 13, 2014

(65) Prior Publication Data
US 2015/0238426 A1    Aug. 27, 2015

(30) Foreign Application Priority Data

Sep. 5, 2012    (JP) ................................. 2012-194894
Feb. 13, 2013    (JP) ................................. 2013-025656

(51) Int. Cl.
| | |
|---|---|
| *A61K 9/20* | (2006.01) |
| *B29C 43/00* | (2006.01) |
| *A61K 31/7024* | (2006.01) |
| *A61K 9/00* | (2006.01) |
| *A61K 9/16* | (2006.01) |
| *B29K 1/00* | (2006.01) |
| *B29L 31/00* | (2006.01) |

(52) U.S. Cl.
CPC ........... *A61K 9/2095* (2013.01); *A61K 9/0056* (2013.01); *A61K 9/1617* (2013.01); *A61K 9/2018* (2013.01); *A61K 9/2027* (2013.01); *A61K 9/2054* (2013.01); *A61K 31/7024* (2013.01); *B29C 43/006* (2013.01); *B29K 2001/00* (2013.01); *B29L 2031/7728* (2013.01)

(58) Field of Classification Search
CPC ............. A61K 9/0056; A61K 9/2018; A61K 9/1617; A61K 9/2027; A61K 9/2095; A61K 31/7024; B29C 43/006; B29C 2001/00
See application file for complete search history.

(56) References Cited

U.S. PATENT DOCUMENTS

| | | | |
|---|---|---|---|
| 5,466,464 A | 11/1995 | Masaki et al. | |
| 2007/0196491 A1* | 8/2007 | Venkatesh ............ | A61K 9/2077 424/480 |
| 2010/0286286 A1* | 11/2010 | Ikeda ................... | A61K 9/0056 514/770 |

FOREIGN PATENT DOCUMENTS

| | | |
|---|---|---|
| EP | 2 161 021 | 3/2010 |
| EP | 2 251 005 | 11/2010 |
| EP | 2 371 358 | 10/2011 |
| JP | 7-187993 | 7/1995 |
| JP | 8-291051 | 11/1996 |
| JP | 2807346 | 7/1998 |
| JP | 2919771 | 4/1999 |
| JP | 2000-247873 | 9/2000 |
| WO | 02/070021 | 9/2002 |

OTHER PUBLICATIONS

English translation of the International Preliminary Report on Patentability and Written Opinion issued Mar. 19, 2015 in PCT/JP2013/073808.
International Search Report issued Feb. 18, 2014 in International (PCT) Application No. PCT/JP2013/073808.
Extended European Search Report issued Feb. 8, 2016 in corresponding European Application No. 13836167.0.

* cited by examiner

*Primary Examiner* — Mina Haghighatian
(74) *Attorney, Agent, or Firm* — Wenderoth, Lind & Ponack, L.L.P.

(57) ABSTRACT

The use of a granular material which is for orally fast disintegrating tablets and comprises at least one kind of water soluble polymer and tannic acid allows production of tablets that can be produced by a simple process with simple production equipment, disintegrate fast in the mouth, and have a proper level of moldability for practical use. The at least one kind of water soluble polymer is preferably selected from the group consisting of povidone, hydroxypropyl cellulose, pullulan, a polyvinyl alcohol-polyethylene glycol graft copolymer and copolyvidone.

18 Claims, No Drawings

GRANULAR MATERIAL FOR ORALLY FAST DISINTEGRATING TABLETS

TECHNICAL FIELD

The present invention relates to a granular material for orally fast disintegrating tablets which disintegrate fast and well in the presence of saliva or a small amount of water in the mouth; an orally fast disintegrating tablet containing the granular material; and a method for producing the orally fast disintegrating tablet.

BACKGROUND ART

Generally known dosage forms for oral solid preparations include tablets, capsules, granules and powders. However, these dosage forms are largely hard to handle and ingest. For example, tablets and capsules have a problem in that larger ones are harder to swallow, and granules and powders also have a problem in that they are easy to choke on and likely to get stuck between the teeth upon their ingestion. In addition, these dosage forms need to be taken with some water, and thus have difficulty in ingestion in the case of an emergency and for bedridden patients with severe illness.

Known dosage forms that can be taken without water include chewable tablets, which are designed to be ingested by chewing. Currently available chewable tablets have poor disintegrability and thus are hard to take for elderly people, children, preschool children, patients with dysphagia, bedridden patients and others.

Under such circumstances, there is a desire for the development of orally fast disintegrating tablets which can be easily taken without water and can be conveniently taken anytime and anywhere.

Known techniques for producing such orally fast disintegrating tablets include a method involving filling a mold (resin film sheet for PTP) with a suspension of an active ingredient and a saccharide in an aqueous agar solution, and solidifying the suspension into a jelly-like form, followed by reduced pressure drying or aeration drying (Patent Literature 1); and a method involving compressing tablet materials in a dry state containing a pharmaceutical agent, a water soluble binder and a water soluble excipient with a minimum pressure necessary for formation of tablets having a hardness enough to keep their shapes during the transition to the next step, wetting the resulting tablets, and drying the wet tablets (Patent Literature 2).

However, these methods are disadvantageous because they require special production equipment and thus are complicated as a production process.

Under such circumstances, there is a desire for the development of preparations that are producible by a simple process with simple production equipment, excellent in oral disintegrability, and practically satisfactory in moldability.

CITATION LIST

Patent Literature

Patent Literature 1: U.S. Pat. No. 2,807,346
Patent Literature 2: U.S. Pat. No. 2,919,771

SUMMARY OF INVENTION

Technical Problem

Therefore, an object of the present invention is to provide an orally fast disintegrating tablet that can be produced by a simple process with simple production equipment, disintegrates fast in the mouth, and has a proper level of moldability for practical use; a method for producing the orally fast disintegrating tablet; and a granular material used as a component of the orally fast disintegrating tablet.

Solution to Problem

The present inventors have conducted extensive research to achieve the above-mentioned object, and as a result, have found that compression molding of a granular material comprising at least one kind of water soluble polymer and tannic acid, or compression molding of this granular material with a binder and/or a disintegrant if needed, allows production of orally fast disintegrating tablets by a simple process without the use of any special production equipment and that the resulting orally fast disintegrating tablets are equivalent or superior in both disintegrability and moldability to conventional orally fast disintegrating tablets.

The present invention has been completed based on this finding, and provides the following granular material for orally fast disintegrating tablets, the following orally fast disintegrating tablet, and the following method for producing an orally fast disintegrating tablet.

(1) A granular material for orally fast disintegrating tablets, the granular material comprising (a) at least one kind of water soluble polymer and (b) tannic acid.

(2) The granular material for orally fast disintegrating tablets according to the above (1), wherein the at least one kind of water soluble polymer is selected from the group consisting of povidone, hydroxypropyl cellulose, pullulan, a polyvinyl alcohol-polyethylene glycol graft copolymer and copolyvidone.

(3) The granular material for orally fast disintegrating tablets according to the above (1) or (2), wherein the content of the ingredient (a) is 0.001 to 60% by weight relative to the total weight of the granular material.

(4) The granular material for orally fast disintegrating tablets according to any of the above (1) to (3), wherein the content of the ingredient (b) is 0.001 to 60% by weight relative to the total weight of the granular material.

(5) The granular material for orally fast disintegrating tablets according to any of the above (1) to (4), further comprising an excipient.

(6) The granular material for orally fast disintegrating tablets according to the above (5), wherein the excipient is at least one kind selected from the group consisting of mannitol and lactose hydrate.

(7) An orally fast disintegrating tablet containing the granular material according to any of the above (1) to (6).

(8) The orally fast disintegrating tablet according to the above (7), further containing a binder and/or a disintegrant.

(9) The orally fast disintegrating tablet according to the above (8), wherein the binder is at least one kind selected from the group consisting of magnesium aluminometasilicate, synthetic aluminum silicate, light silicic acid anhydride, calcium silicate and crystalline cellulose.

(10) The orally fast disintegrating tablet according to the above (8) or (9), wherein the disintegrant is at least one kind selected from the group consisting of crospovidone, carmellose, carmellose calcium, croscarmellose sodium and low-substituted hydroxypropyl cellulose.

(11) The orally fast disintegrating tablet according to any of the above (7) to (10), having a disintegration time of 30 seconds or less as measured by a disintegration test specified in the Japanese Pharmacopoeia.

(12) The orally fast disintegrating tablet according to any of the above (7) to (11), having a hardness of 5 kgf or more.
(13) A method for producing an orally fast disintegrating tablet, comprising compression molding of
   (A) the granular material according to any of the above (1) to (6), or
   (B) a mixture of the granular material according to any of the above (1) to (6), and an additive and/or a pharmaceutically active ingredient.
(14) The method according to the above (1.3), wherein the additive is a binder and/or a disintegrant.

Advantageous Effects of Invention

The orally fast disintegrating tablet of the present invention is excellent in oral disintegrability as well as having a proper level of moldability, and thus is excellent in terms of the ease of ingestion.

DESCRIPTION OF EMBODIMENTS

Hereinafter, the present invention will be explained in detail.
(I) Granular Material for Orally Fast Disintegrating Tablets
The granular material of the present invention for orally fast disintegrating tablets is intended to be used for orally fast disintegrating tablets, and comprises (a) at least one kind of water soluble polymer and (b) tannic acid.
In the present invention, "for orally fast disintegrating tablets" refers to having an application as a material for constituting or producing orally fast disintegrating tablets.
Ingredient (a)
The water soluble polymer is not particularly limited as long as it can be used in the field of the formulation of pharmaceutical and food preparations etc. Examples of the water soluble polymer include cellulose-based polymers such as methyl cellulose, ethyl cellulose, hydroxyethyl cellulose, hydroxypropylmethylcellulose phthalate, hydroxypropyl cellulose, hydroxypropylmethylcellulose and their pharmaceutically acceptable salts; polyvinyl-based polymers such as povidone, polyvinyl alcohol (including partially or fully saponified polyvinyl alcohol), a polyvinyl alcohol-polyethylene glycol graft copolymer and copolyvidone; polysaccharides such as pullulan, dextrin, partially pregelatinized starch, alginic acid, sodium alginate, agar, gum arabic and xanthan gum; and gelatin.
The water soluble polymer used may be of one kind or any combination of two or more kinds.
Particularly preferable water soluble polymers include povidone, hydroxypropyl cellulose, pullulan, a polyvinyl alcohol-polyethylene glycol graft copolymer and copolyvidone.
The type of povidone is not particularly limited and any type of povidone usable in the field of the formulation of pharmaceutical and food preparations etc. may be used. Examples of such povidone include Plasdone K-25 (K-value: 25), Plasdone K-29/32 (K-value: 29 to 32), Plasdone K-90 (K-value: 90), Plasdone K-900 (K-value: 90) and Plasdone K-90M (K-value: 90) (all of them are trade names and available from ISP Japan Ltd.); and Kollidon 25 (K-value: 25), Kollidon 30 (K-value: 30) and Kollidon 90F (K-value: 90) (all of them are trade names and available from BASF Japan Ltd.).
The type of hydroxypropyl cellulose is not particularly limited and any type of hydroxypropyl cellulose usable in the field of the formulation of pharmaceutical and food preparations etc. may be used. Examples of such hydroxypropyl cellulose include HPC-SSL (viscosity: 2.0 to 2.9 mPa·s), HPC-SL (viscosity: 3.0 to 5.9 mPa·s), HPC-L (viscosity: 6.0 to 10.0 mPa·s), HPC-M (viscosity: 150 to 400 mPa·s) and HPC-H (viscosity: 1000 to 4000 mPa·s) (all of them are trade names and available from Nippon Soda Co., Ltd.).
The type of pullulan is not particularly limited and any type of pullulan usable in the field of the formulation of pharmaceutical and food preparations etc. may be used. Examples of such pullulan include a product available as the trade name "pullulan" from Hayashibara Co., Ltd.
The type of polyvinyl alcohol-polyethylene glycol graft copolymer is not particularly limited and any type of polyvinyl alcohol-polyethylene glycol graft copolymer usable in the field of the formulation of pharmaceutical and food preparations etc. may be used. Examples of such a polyvinyl alcohol polyethylene glycol graft copolymer include Kollicoat IR (trade name and available from BASF Japan Ltd.).
The type of copolyvidone is not particularly limited and any type of copolyvidone usable in the field of the formulation of pharmaceutical and food preparations etc. may be used. Examples of such copolyvidone include Kollidon VA64 (trade name and available from BASF Japan Ltd.) and Plasdone S-630 (trade name and available from ISP Japan Ltd.).
The amount of the ingredient (a) in the granular material is preferably about 0.001% by weight or more, more preferably about 0.01% by weight or more, and still more preferably about 0.1% by weight or more relative to the total weight of the granular material. When the amount of the ingredient (a) is as above, tablets produced from the granular material of the present invention have sufficient moldability. In addition, the amount of the ingredient (a) is preferably about 60% by weight or less, more preferably about 30% by weight or less, and still more preferably about 10% by weight or less. When the amount of the ingredient (a) is as above, tablets produced from the granular material of the present invention have sufficient disintegrability.
Ingredient (b)
Tannic acid can be extracted from various kinds of vegetable sources. For example, tannic acid can be extracted with water or ethanol from persimmon fruit, chestnut astringent skin, *Rhus chinensis* galls (*Galla chinensis*), *Quercus infectoria* galls, Tara powder, tamarind (family Fabaceae) seed coat, mimosa bark, etc. The tannic acid extracted from *Rhus chinensis* galls or *Quercus infectoria* galls as specified in the Japanese Pharmacopoeia, 16th edition is preferably used. The tannic acid used may be in an unpurified or purified state, but preferably in a purified state.
The amount of tannic acid as the ingredient (b) in the granular material is preferably about 0.001% by weight or more, more preferably about 0.01% by weight or more, and still more preferably about 0.1% by weight or more relative to the total weight of the granular material. When the amount of the ingredient (b) is as above, tablets produced from the granular material of the present invention have sufficient disintegrability. In addition, the amount of the ingredient (b) is preferably 60% by weight or less, more preferably about 30% by weight or less, and still more preferably about 10% by weight or less. When the amount of the ingredient (b) is as above, tablets produced from the granular material of the present invention have sufficient moldability.
The content ratio of the ingredients (a) and (b) (ingredients (a):(b)) is preferably about 1:0.001 to 1000, more preferably about 1:0.01 to 100, and still more preferably about 1:0.1 to 10. When the content ratio of the ingredients (a) and (b) is in this range, a sufficient level of moldability and disintegrability can be achieved.

Other Ingredients

The granular material desirably comprises, in addition to the above-described ingredients (a) and (b), an excipient as an additive. Tablets produced from such a granular material have further improved moldability and disintegrability.

Examples of the excipient include sugar alcohols such as mannitol, sorbitol, xylitol, erythritol, maltitol and isomalt; saccharides such as lactose hydrate, anhydrous lactose, sucrose, purified sucrose, fructose, glucose, glucose hydrate and trehalose; starches such as corn starch, potato starch, wheat starch and rice starch; amino acids such as glycine and alanine; silicic acid compounds such as light silicic acid anhydride, synthetic aluminum silicate, magnesium aluminometasilicate and calcium silicate; cellulosic compounds such as crystalline cellulose and powdered cellulose; talc; and titanium oxide. For fast disintegration of the granular material in the mouth, preferred are sugar alcohols and saccharides, and among them, particularly preferred are mannitol and lactose hydrate.

The excipient used may be of one kind or any combination of two or more kinds.

The granular material can further comprise an appropriate amount of another additive commonly used in pharmaceuticals, such as a lubricant, a colorant, a corrigent, a sweetener, a flavoring agent and a preservative.

Examples of the lubricant include magnesium stearate, calcium stearate, talc, sucrose fatty acid ester and sodium stearyl fumarate.

Examples of the colorant include food dyes, food lake dyes, red ferric oxide and yellow ferric oxide.

Examples of the corrigent include citric acid hydrate, tartaric acid, malic acid and ascorbic acid.

Examples of the sweetener include aspartame, acesulfame potassium, saccharin, sodium saccharin, dipotassium glycyrrhizinate, stevia, thaumatin and sucralose.

Examples of the flavoring agent include fennel oil, orange oil, German chamomile oil, spearmint oil, cinnamon oil, clove oil, mentha oil, bergamot oil, eucalyptus oil, lavender oil, lemon oil, rose oil, Roman chamomile oil and menthol.

Examples of the preservative include benzoic acid, sodium benzoate, benzyl benzoate, isobutyl p-hydroxybenzoate, isopropyl p-hydroxybenzoate, ethyl p-hydroxybenzoate, butyl p-hydroxybenzoate, propyl p-hydroxybenzoate, propyl p-hydroxybenzoate sodium salt, methyl p-hydroxybenzoate and methyl p-hydroxybenzoate sodium salt.

The additive used may be of one kind or any combination of two or more kinds.

The granular material can comprise an appropriate amount of a pharmaceutically active ingredient. The pharmaceutically active ingredient is not particularly limited in terms of its type and amount as long as the type and amount of the pharmaceutically active ingredient do not impair the disintegrability or moldability of orally fast disintegrating tablets containing the granular material.

Granulation

The granulation process to prepare a granular material comprising the above-described ingredients is, for example, a wet granulation process, a dry granulation process, a fluid bed granulation process, or the like, and in particular, a wet granulation process is preferable because of its convenience.

The wet granulation process involves kneading the ingredients and a solvent and then granulating the resulting wet mass. This process can utilize the protocol and equipment used in grinding granulation, extrusion granulation, agitation granulation, tumbling granulation, etc. for the production of ordinary preparations. The solvent that can be used in this process is a solvent used for the production of ordinary preparations, such as alcohols such as ethanol and isopropanol, and water.

The dry granulation process involves uniformly mixing all the ingredients and then granulating the mixture. This process can utilize the protocol and equipment used in compression granulation etc. for the production of ordinary preparations.

The fluid bed granulation process involves spraying a solvent alone or a solvent mixed with a binder etc. to the ingredients for granular formation. This process can utilize the protocol and equipment used in fluid bed granulation etc. for the production of ordinary preparations.

(II) Orally Fast Disintegrating Tablet

Tableting

For production of the orally fast disintegrating tablet of the present invention (hereinafter also called "the tablet of the present invention") from the above-described granular material, the granular material of the present invention is mixed with other ingredients such as a binder and a disintegrant as appropriate, and the mixture is then subjected to compression molding.

The compression molding can utilize the protocol and equipment used for the molding of ordinary tablets in a rotary tablet press, a single punch tablet press, etc. The compression pressure in the compression molding is preferably about 100 $kgf/cm^2$ or more, more preferably about 200 $kgf/cm^2$ or more, and still more preferably about 400 $kgf/cm^2$ or more. In addition, the compression pressure is preferably 6000 $kgf/cm^2$ or less, more preferably about 3000 $kgf/cm^2$ or less, and still more preferably about 1500 $kgf/cm^2$ or less. When the compression pressure is in the above range, the load imposed on the dies and punches during the tableting operation is reduced and the tableting pressure is easy to keep constant during the tableting operation.

The compression molding of the granular material may be preceded by other procedures required for tablet production, for example, drying with a fluid bed dryer, a shelf dryer or the like; particle size adjustment with a screen mill, a jet mill, a hammer mill, a pin mill or the like; sieving with a vibrating sieve; etc.

The tablet of the present invention can substantially be composed of only the above-described granular material of the present invention, but an additional ingredient such as a binder and a disintegrant can also be contained in the tablet.

Regardless of the presence or absence of the additional ingredient, the amount of the granular material in the tablet of the present invention is preferably about 10% by weight or more, more preferably about 30% by weight or more, and still more preferably about 60% by weight or more relative to the total weight of the tablet. That is, in the case where the tablet of the present invention contains an ingredient(s) other than the granular material, the total amount of the ingredient(s) other than the granular material is preferably about 90% by weight or less, more preferably about 70% by weight or less, and still more preferably about 40% by weight or less relative to the total weight of the tablet. When the amounts of the ingredients are as above, a practically sufficient level of moldability and disintegrability can be achieved.

Since the tablet of the present invention is produced by compression molding, the shape of the granular material present in the tablet is usually different from the original shape of the granular material.

Binder

The tablet of the present invention can contain a binder. Binders serve to combine granular materials together under compression.

Examples of the binder include magnesium aluminometasilicate, synthetic aluminum silicate, light silicic acid anhydride, calcium silicate, crystalline cellulose, powdered cellulose and low-substituted hydroxypropyl cellulose. In particular, magnesium aluminometasilicate, synthetic aluminum silicate, light silicic acid anhydride, calcium silicate and crystalline cellulose are preferable.

The amount of the binder is preferably about 0.01% by weight or more, more preferably about 0.1% by weight or more, and still more preferably about 1% by weight or more relative to the total weight of the tablet. In addition, the amount of the binder is preferably about 30% by weight or less, more preferably about 20% by weight or less, and still more preferably about 10% by weight or less relative to the total weight of the tablet. When the amount of the binder is in the above range, a practically sufficient level of moldability and disintegrability can be achieved.

The binder used may be of one kind or any combination of two or more kinds.

Disintegrant

The tablet of the present invention can contain a disintegrant. Disintegrants are ingredients which absorb water and subsequently swell, or ingredients which absorb water and thereby facilitate the breakup of the composition.

Examples of the disintegrant include crospovidone, carmellose calcium, carmellose, alginic acid, croscarmellose sodium, low-substituted hydroxypropyl cellulose, corn starch, potato starch, wheat starch, rice starch, partially pregelatinized starch, pregelatinized starch and sodium carboxymethyl starch. In particular, crospovidone, carmellose, carmellose calcium, croscarmellose sodium and low-substituted hydroxypropyl cellulose are preferable.

The amount of the disintegrant is preferably about 0.01% by weight or more, more preferably about 0.1% by weight or more, and still more preferably about 1% by weight or more relative to the total weight of the tablet. In addition, the amount of the disintegrant is preferably about 30% by weight or less, more preferably about 20% by weight or less, and still more preferably about 10% by weight or less relative to the total weight of the tablet. When the amount of the disintegrant is in the above range, a practically sufficient level of moldability and disintegrability can be achieved.

The disintegrant used may be of one kind or any combination of two or more kinds.

Other Ingredients

The tablet of the present invention can further contain an appropriate amount of another additive commonly used in pharmaceuticals, such as an excipient, a lubricant, a colorant, a corrigent, a sweetener, a flavoring agent and a preservative. A pharmaceutically active ingredient can also be contained in the tablet.

The additive used may be of one kind or any combination of two or more kinds. The pharmaceutically active ingredient used may be of one kind or any combination of two or more kinds.

The thus obtained tablets have a proper level of moldability for practical use, and also are excellent in oral disintegrability.

The disintegration time of the tablet of the present invention, as measured according to the disintegration test specified in the manual of the Japanese Pharmacopoeia, 16th edition (in particular, using a disintegration tester (manufactured by Toyama Sangyo Co., Ltd.)), is preferably 30 seconds or less, more preferably 20 seconds or less, and still more preferably 10 seconds or less.

The hardness of the tablet of the present invention (in particular, the hardness as measured using a tablet hardness tester (manufactured by Toyama Sangyo Co., Ltd.)) is preferably 5 kgf or more, more preferably 6 kgf or more, and still more preferably 7 kgf or more.

EXAMPLES

Hereinafter, the present invention will be illustrated in more detail by examples and comparative examples, but is not limited to these examples.
(1) Physical Property Testing
<Disintegration Test>

The test was performed based on the disintegration test specified in the manual of the Japanese Pharmacopoeia, 16th edition using a disintegration tester (manufactured by Toyama Sangyo Co., Ltd.). The disintegration time was measured for 6 tablets per sample and the mean was evaluated.
<Hardness Test>

The test was performed using a tablet hardness tester (manufactured by Toyama Sangyo Co., Ltd.). The hardness was measured for 10 tablets per sample and the mean was evaluated.
(2) Tablet Production Examples 1 and 2

Based on the composition shown in Table 1 below, firstly ingredient (a) and mannitol were fed into a stirring granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Examples 1 and 2

Based on the composition shown in Table 1 below, firstly ingredient (a) and mannitol were fed into a stirring and mixing granulator and mixed, and then an appropriate amount of ethanol as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 3

Based on the composition shown in Table 1 below, firstly mannitol was fed into a stirring and mixing granulator, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Comparative Example 4

Based on the composition shown in Table 1 below, firstly mannitol was fed into a stirring and mixing granulator, and then an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Examples 3 and 4

Based on the composition shown in Table 2 below, firstly ingredient (a) and lactose hydrate were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than lactose hydrate were added, and the whole was mixed and fed into a tablet press, in which the mixture was then compressed at a tabletting pressure of about 800 kgf/cm² into tablets each having a diameter of 8.5 mm and a mass of 240 mg.

Examples 5 to 10

Based on the composition shown in Table 2 below, firstly ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Examples 11 and 12

Based on the composition shown in Table 3 below, firstly a pharmaceutically active ingredient (meclizine hydrochloride), ingredient (a) and mannitol were fed into a stirring and mixing granulator and mixed, and then a solution of the other pharmaceutically active ingredient (scopolamine hydrobromide hydrate) and ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Examples 13 to 16

Based on the composition shown in Table 3 below, firstly a pharmaceutically active ingredient, ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Examples 17 and 18

Based on the composition shown in Table 3 below, firstly ingredient (a) and mannitol were fed into a stirring and mixing granulator and mixed, and then a solution of a pharmaceutically active ingredient and ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Comparative Examples 5 and 6

Based on the composition shown in Table 4 below, firstly a pharmaceutically active ingredient (meclizine hydrochloride), ingredient (a) and mannitol were fed into a stirring and mixing granulator and mixed, and then a solution of the other pharmaceutically active ingredient (scopolamine hydrobromide hydrate) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Comparative Examples 7 to 10

Based on the composition shown in Table 4 below, firstly a pharmaceutically active ingredient, ingredient (a) and mannitol were fed into a stirring and mixing granulator and mixed, and then an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tabletting pressure of about 800 kgf/cm² into tablets each having a diameter of 8.5 mm and a mass of 240 mg.

Comparative Examples 11 and 12

Based on the composition shown in Table 4 below, firstly ingredient (a) and mannitol were fed into a stirring and mixing granulator and mixed, and then a solution of a pharmaceutically active ingredient in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 19

Based on the composition shown in Table 5 below, firstly ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 20

Based on the composition shown in Table 5 below, firstly ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 13

Based on the composition shown in Table 5 below, firstly ingredient (a) and mannitol were fed into a stirring and mixing granulator and mixed, and then an appropriate amount of ethanol as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 14

Based on the composition shown in Table 5 below, firstly ingredient (a) and mannitol were fed into a stirring and mixing granulator and mixed, and then an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 15

Based on the composition shown in Table 5 below, firstly mannitol was fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 16

Based on the composition shown in Table 5 below, firstly mannitol was fed into a stirring and mixing granulator and mixed, and then an appropriate amount of ethanol as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 17

Based on the composition shown in Table 5 below, firstly mannitol was fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 18

Based on the composition shown in Table 5 below, firstly mannitol was fed into a stirring and mixing granulator and mixed, and then an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the formulation bases other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 21

Based on the composition shown in Table 6 below, firstly ingredient (a) and lactose hydrate were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 22

Based on the composition shown in Table 6 below, firstly ingredient (a) and lactose hydrate were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 23

Based on the composition shown in Table 6 below, firstly ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 24

Based on the composition shown in Table 6 below, firstly ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 25

Based on the composition shown in Table 6 below, firstly ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 26

Based on the composition shown in Table 6 below, firstly ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 27

Based on the composition shown in Table 6 below, firstly ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 28

Based on the composition shown in Table 6 below, firstly ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 29

Based on the composition shown in Table 7 below, firstly a pharmaceutically active ingredient (meclizine hydrochloride), ingredient (a) and mannitol were fed into a stirring and mixing granulator and mixed, and then a solution of the other pharmaceutically active ingredient (scopolamine hydrobromide hydrate) and ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was

Example 30

Based on the composition shown in Table 7 below, firstly a pharmaceutically active ingredient (meclizine hydrochloride), ingredient (a) and mannitol were fed into a stirring and mixing granulator and mixed, and then a solution of the other pharmaceutically active ingredient (scopolamine hydrobromide hydrate) and ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 31

Based on the composition shown in Table 7 below, firstly a pharmaceutically active ingredient, ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 32

Based on the composition shown in Table 7 below, firstly a pharmaceutically active ingredient, ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 33

Based on the composition shown in Table 7 below, firstly a pharmaceutically active ingredient, ingredient (a) and mannitol were fed into a stirring and mixing granulator and mixed, and then a solution of ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 34

Based on the composition shown in Table 7 below, firstly a pharmaceutically active ingredient, ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 35

Based on the composition shown in Table 7 below, firstly ingredient (a) and mannitol were fed into a stirring and mixing granulator and mixed, and then a solution of a pharmaceutically active ingredient and ingredient (b) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Example 36

Based on the composition shown in Table 7 below, firstly a pharmaceutically active ingredient, ingredient (a) and mannitol were fed into a stirring and mixing granulator and mixed, and then a solution of ingredient (b) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 19

Based on the composition shown in Table 8 below, firstly a pharmaceutically active ingredient (meclizine hydrochloride), ingredient (a) and mannitol were fed into a stirring and mixing granulator and mixed, and then a solution of the other pharmaceutically active ingredient (scopolamine hydrobromide hydrate) in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 20

Based on the composition shown in Table 8 below, firstly a pharmaceutically active ingredient (meclizine hydrochloride), ingredient (a) and mannitol were fed into a stirring and mixing granulator and mixed, and then a solution of the other pharmaceutically active ingredient (scopolamine hydrobromide hydrate) in an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 21

Based on the composition shown in Table 8 below, firstly a pharmaceutically active ingredient, ingredient (a) and mannitol were fed into a stirring and mixing granulator and mixed, and then an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 22

Based on the composition shown in Table 8 below, firstly a pharmaceutically active ingredient, ingredient (a) and mannitol were fed into a stirring and mixing granulator and mixed, and then an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 23

Based on the composition shown in Table 8 below, firstly a pharmaceutically active ingredient, ingredient (a) and mannitol were fed into a stirring and mixing granulator and mixed, and then an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 24

Based on the composition shown in Table 8 below, firstly a pharmaceutically active ingredient, ingredient (a) and mannitol were fed into a stirring and mixing granulator and mixed, and then an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 25

Based on the composition shown in Table 8 below, firstly ingredient (a) and mannitol were fed into a stirring and mixing granulator and mixed, and then a solution of a pharmaceutically active ingredient in an appropriate amount of ethanol as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

Comparative Example 26

Based on the composition shown in Table 8 below, firstly a pharmaceutically active ingredient, ingredient (a) and mannitol were fed into a stirring and mixing granulator and mixed, and then an appropriate amount of a water/ethanol mixture (17:3) as a granulation solvent was gradually added to give granules. Next, the granules were dried in a shelf dryer, and the dried granules were subjected to particle size adjustment. To the uniformly sized granules, the additives other than mannitol were added, and the whole was mixed and fed into a tablet press, in which the mixture was then compressed at a tableting pressure of about 800 kgf/cm$^2$ into tablets each having a diameter of 8.5 mm and a mass of 240 mg.

(3) Results

The compositions of the tablets of Examples 1 and 2 and Comparative Examples 1 to 4, and their test results for disintegration and hardness are shown in the following Table 1.

TABLE 1

| | | (Unit of amount: g) | | | | | |
|---|---|---|---|---|---|---|---|
| Ingredients | | Example 1 | Example 2 | Comparative Example 1 | Comparative Example 2 | Comparative Example 3 | Comparative Example 4 |
| (a) | Povidone (K30) | 12.0 | | 12.0 | | | |
| | Hydroxypropyl cellulose (HPC-L) | | 12.0 | | 12.0 | | |

TABLE 1-continued (Unit of amount: g)

| Ingredients | | Example 1 | Example 2 | Comparative Example 1 | Comparative Example 2 | Comparative Example 3 | Comparative Example 4 |
|---|---|---|---|---|---|---|---|
| (b) Additives | Tannic acid | 6.0 | 6.0 | | | 6.0 | |
| | Mannitol (excipient) | 510.6 | 510.6 | 516.6 | 516.6 | 522.6 | 528.6 |
| | Magnesium aluminometasilicate (binder) | 9.0 | 9.0 | 9.0 | 9.0 | 9.0 | 9.0 |
| | Crospovidone (disintegrant) | 30.0 | 30.0 | 30.0 | 30.0 | 30.0 | 30.0 |
| | Aspartame (sweetener) | 1.8 | 1.8 | 1.8 | 1.8 | 1.8 | 1.8 |
| | L-menthol (refrigerant) | 0.6 | 0.6 | 0.6 | 0.6 | 0.6 | 0.6 |
| | Citric acid hydrate (corrigent) | 3.0 | 3.0 | 3.0 | 3.0 | 3.0 | 3.0 |
| | Magnesium stearate (lubricant) | 3.0 | 3.0 | 3.0 | 3.0 | 3.0 | 3.0 |
| | Total amount (g) | 576.0 | 576.0 | 576.0 | 576.0 | 576.0 | 576.0 |
| Physical property values | Hardness (mean) (kgf) | 5.37 | 5.21 | 6.46 | 6.51 | 4.36 | 1.55 |
| | Disintegration time (mean) (second) | 8 | 8 | 40 | 19 | 9 | 8 |

As clearly shown in Table 1, the tablets of Examples 1 and 2 had a disintegration time of 8 seconds each and a hardness of 5.37 kgf and 5.21 kgf, respectively, and were excellent in disintegrability and moldability. In contrast, the tablets of Comparative Examples 1 and 2, which did not contain tannic acid as the ingredient (b), had a disintegration time of 40 seconds and 19 seconds, respectively, and were inferior in disintegrability to the tablets of Examples 1 and 2. The tablet of Comparative Example 3, which did not contain povidone or hydroxypropyl cellulose as the ingredient (a), had a hardness of 4.36 kgf, and was inferior in moldability to the tablets of Examples 1 and 2, and molding failure was observed. The tablet of Comparative Example 4, which did not contain the ingredient (a) or (b), had a hardness of 1.55 kgf, and was further inferior in moldability to the tablets of Examples 1 and 2, and molding failure was observed.

The compositions of the tablets of Examples 3 to 10, and their test results for disintegration and hardness are shown in the following Table 2.

TABLE 2

(Unit of amount: g)

| Ingredients | | | Example 3 | Example 4 | Example 5 | Example 6 | Example 7 | Example 8 | Example 9 | Example 10 |
|---|---|---|---|---|---|---|---|---|---|---|
| (a) | Povidone (K30) | | 12.0 | | 12.0 | | 12.0 | | 12.0 | |
| | Hydroxypropyl cellulose (HPC-L) | | | 12.0 | | 12.0 | | 12.0 | | 12.0 |
| (b) | Tannic acid | | 6.0 | 6.0 | 6.0 | 6.0 | 6.0 | 6.0 | 6.0 | 6.0 |
| Additives | Excipients | Mannitol | | | 510.6 | 510.6 | 510.6 | 510.6 | 510.6 | 510.6 |
| | | Lactose hydrate | 510.6 | 510.6 | | | | | | |
| | Binders | Magnesium aluminometasilicate | 9.0 | 9.0 | | | | | | |
| | | Synthetic aluminum silicate | | | 9.0 | 9.0 | | | | |
| | | Light silicic acid anhydride | | | | | 9.0 | 9.0 | | |
| | | Calcium silicate | | | | | | | 9.0 | 9.0 |
| | Crospovidone (disintegrant) | | 30.0 | 30.0 | 30.0 | 30.0 | 30.0 | 30.0 | 30.0 | 30.0 |
| | Aspartame (sweetener) | | 1.8 | 1.8 | 1.8 | 1.8 | 1.8 | 1.8 | 1.8 | 1.8 |
| | L-menthol (refrigerant) | | 0.6 | 0.6 | 0.6 | 0.6 | 0.6 | 0.6 | 0.6 | 0.6 |
| | Citric acid hydrate (corrigent) | | 3.0 | 3.0 | 3.0 | 3.0 | 3.0 | 3.0 | 3.0 | 3.0 |
| | Magnesium stearate (lubricant) | | 3.0 | 3.0 | 3.0 | 3.0 | 3.0 | 3.0 | 3.0 | 3.0 |
| | Total amount (g) | | 576.0 | 576.0 | 576.0 | 576.0 | 576.0 | 576.0 | 576.0 | 576.0 |
| Physical property values | Hardness (mean) (kgf) | | 5.43 | 6.00 | 6.89 | 6.92 | 6.41 | 6.80 | 6.45 | 6.24 |
| | Disintegration time (mean) (second) | | 11 | 8 | 11 | 9 | 12 | 9 | 11 | 11 |

As is clear from the test results in Table 2, the tablets of Examples 3 to 10 had a disintegration time of 8 to 12 seconds and a hardness of 5.43 to 6.92 kgf, and were excellent in disintegrability and moldability.

The compositions of the tablets of Examples 11 to 18 and Comparative Examples 5 to 12, and their test results for disintegration and hardness are shown in the following Tables 3 and 4.

TABLE 3

(Unit of amount: g)

| Ingredients | | Example 11 Meclizine hydrochloride 30.0 | Example 12 Scopolamine hydrobromide hydrate | Example 13 | Example 14 Famotidine | Example 15 | Example 16 Ketotifen fumarate | Example 17 | Example 18 Loperamide hydrochloride |
|---|---|---|---|---|---|---|---|---|---|
| Pharmaceutically active ingredients | | 0.3 | | 24.0 | | 3.312 | | 1.2 | |
| (a) | Povidone (K30) | 12.0 | | 12.0 | | 12.0 | | 12.0 | |
| | Hydroxypropyl cellulose (HPC-L) | | 12.0 | | 12.0 | | 12.0 | | 12.0 |
| (b) Additive | Tannic acid | 6.0 | 6.0 | 6.0 | 6.0 | 6.0 | 6.0 | 6.0 | 6.0 |
| | Mannitol (excipient) | 480.3 | 480.3 | 486.6 | 486.6 | 507.288 | 507.288 | 509.4 | 509.4 |
| | Magnesium aluminometasilicate binder) | 9.0 | 9.0 | 9.0 | 9.0 | 9.0 | 9.0 | 9.0 | 9.0 |
| | Crospovidone (disintegrant) | 30.0 | 30.0 | 30.0 | 30.0 | 30.0 | 30.0 | 30.0 | 30.0 |
| | Aspartame (sweetener) | 1.8 | 1.8 | 1.8 | 1.8 | 1.8 | 1.8 | 1.8 | 1.8 |
| | L-menthol (refrigerant) | 0.6 | 0.6 | 0.6 | 0.6 | 0.6 | 0.6 | 0.6 | 0.6 |
| | Citric acid hydrate (corrigent) | 3.0 | 3.0 | 3.0 | 3.0 | 3.0 | 3.0 | 3.0 | 3.0 |
| | Magnesium stearate (lubricant) | 3.0 | 3.0 | 3.0 | 3.0 | 3.0 | 3.0 | 3.0 | 3.0 |
| | Total amount (g) | 576.0 | 576.0 | 576.0 | 576.0 | 576.0 | 576.0 | 576.0 | 576.0 |
| Physical property values | Hardness (mean) (kgf) | 5.28 | 6.05 | 6.15 | 7.12 | 6.334 | 6.49 | 5.82 | 6.55 |
| | Disintegration time (mean) (second) | 5 | 8 | 12 | 8 | 9 | 8 | 9 | 9 |

TABLE 4

(Unit of amount: g)

| Ingredients | | Comparative Example 5 Meclizine hydrochloride 3.0 | Comparative Example 6 Scopolamine hydrobromide hydrate 0.3 | Comparative Example 7 | Comparative Example 8 Famotidine 24.0 | Comparative Example 9 | Comparative Example 10 Ketotifen fumarate 3.312 | Comparative Example 11 | Comparative Example 12 Loperamide hydrochloride 1.2 |
|---|---|---|---|---|---|---|---|---|---|
| Pharmaceutically active ingredients | | | | | | | | | |
| a) | Povidone (K30) | 12.0 | | 12.0 | | 12.0 | | 12.0 | |
| | Hydroxypropyl cellulose (HPC-L) | | 12.0 | | 12.0 | | 12.0 | | 12.0 |
| b) Additives | Tannic acid | | | | | | | | |
| | Mannitol (excipient) | 486.3 | 486.3 | 492.6 | 492.6 | 513.288 | 513.288 | 515.4 | 515.4 |
| | Magnesium aluminometasilicate (binder) | 9.0 | 9.0 | 9.0 | 9.0 | 9.0 | 9.0 | 9.0 | 9.0 |
| | Crospovidone (disintegrant) | 30.0 | 30.0 | 30.0 | 30.0 | 30.0 | 30.0 | 30.0 | 30.0 |
| | Aspartame (sweetener) | 1.8 | 1.8 | 1.8 | 1.8 | 1.8 | 1.8 | 1.8 | 1.8 |
| | L-menthol (refrigerant) | 0.6 | 0.6 | 0.6 | 0.6 | 0.6 | 0.6 | 0.6 | 0.6 |
| | Citric acid hydrate (corrigent) | 3.0 | 3.0 | 3.0 | 3.0 | 3.0 | 3.0 | 3.0 | 3.0 |
| | Magnesium stearate (lubricant) | 3.0 | 3.0 | 3.0 | 3.0 | 3.0 | 3.0 | 3.0 | 3.0 |
| | Total amount(g) | 576.0 | 576.0 | 576.0 | 576.0 | 576.0 | 576.0 | 576.0 | 576.0 |

TABLE 4-continued (Unit of amount: g)

| Ingredients | | Comparative Example 5 Meclizine hydrochloride 3.0 | Comparative Example 6 Scopolamine hydrobromide hydrate 0.3 | Comparative Example 7 | Comparative Example 8 Famotidine 24.0 | Comparative Example 9 | Comparative Example 10 Ketotifen fumarate 3.312 | Comparative Example 11 | Comparative Example 12 Loperamide hydrochloride 1.2 |
|---|---|---|---|---|---|---|---|---|---|
| Pharmaceutically active ingredients | | | | | | | | | |
| Physical property values | Hardness (mean) (kgf) | 6.40 | 6.56 | 6.49 | 6.86 | 7.02 | 6.02 | 6.67 | 6.97 |
| | Disintegration time (mean) (second) | 40 | 14 | 36 | 15 | 43 | 15 | 35 | 19 |

As is clear from the test results in Table 3, the tablets of Examples 11 to 18 had a disintegration time of 5 to 12 seconds and a hardness of 5.28 to 7.12 kgf, and were excellent in disintegrability and moldability regardless of the kind of the pharmaceutically active ingredient used.

In contrast, as is clear from the test results in Table 4, the tablets of Comparative Examples 5 to 12, which did not contain tannic acid as the ingredient (b), had a disintegration time of 14 to 43 seconds, and were inferior in disintegrability to the tablets of Examples 11 to 18.

The compositions of the tablets of Examples 19 and 20 and Comparative Examples 13 to 18, and their test results for disintegration and hardness are shown in the following Table 5.

respectively, and were excellent in disintegrability and moldability. In contrast, the tablets of Comparative Examples 13 and 14, which did not contain the ingredient (b), had a disintegration time of 41 seconds and 43 seconds, respectively, and were inferior in disintegrability to the tablets of Examples 19 and 20. The tablets of Comparative Examples 15 and 17, which did not contain the ingredient (a), had a hardness of 4.36 kgf and 4.27 kgf, respectively, and were inferior in moldability to the tablets of Examples 19 and 20, and molding failure was observed. The tablets of Comparative Examples 16 and 18, which did not contain the ingredient (a) or (b), had a hardness of 1.55 kgf and 1.68 kgf, respectively, and were further inferior in moldability to the tablets of Examples 19 to 20, and molding failure was observed.

TABLE 5

(Unit of amount: g)

| | | Example 19 | Example 20 | Comparative Example 13 | Comparative Example 14 | Comparative Example 15 | Comparative Example 16 | Comparative Example 17 | Comparative Example 18 |
|---|---|---|---|---|---|---|---|---|---|
| (a) | Copolyvidone (Kollidon VA64) | 12.0 | | 12.0 | | | | | |
| | Polyvinyl alcohol-polyethylene glycol graft copolymer (Kollicoat IR) | | 12.0 | | 12.0 | | | | |
| (b) | Tannic acid | 6.0 | 6.0 | | | 6.0 | | 6.0 | |
| Additives | Mannitol (excipient) | 510.6 | 510.6 | 516.6 | 516.6 | 522.6 | 528.6 | 522.6 | 528.6 |
| | Magnesium aluminometasilicate (binder) | 9.0 | 9.0 | 9.0 | 9.0 | 9.0 | 9.0 | 9.0 | 9.0 |
| | Crospovidone (disintegrant) | 30.0 | 30.0 | 30.0 | 30.0 | 30.0 | 30.0 | 30.0 | 30.0 |
| | Aspartame (sweetener) | 1.8 | 1.8 | 1.8 | 1.8 | 1.8 | 1.8 | 1.8 | 1.8 |
| | L-menthol (refrigerant) | 0.6 | 0.6 | 0.6 | 0.6 | 0.6 | 0.6 | 0.6 | 0.6 |
| | Citric acid hydrate (corrigent) | 3.0 | 3.0 | 3.0 | 3.0 | 3.0 | 3.0 | 3.0 | 3.0 |
| | Magnesium stearate (lubricant) | 3.0 | 3.0 | 3.0 | 3.0 | 3.0 | 3.0 | 3.0 | 3.0 |
| Physical property values | Total amount (g) | 576.0 | 576.0 | 576.0 | 576.0 | 576.0 | 576.0 | 576.0 | 576.0 |
| | Hardness (mean) (kgf) | 5.87 | 6.20 | 5.99 | 7.28 | 4.36 | 1.55 | 4.27 | 1.68 |
| | Disintegration time (mean) (second) | 12 | 16 | 41 | 43 | 9 | 8 | 13 | 12 |

As is clear from the test results in Table 5, the tablets of Examples 19 and 20 had a disintegration time of 12 seconds and 16 seconds and a hardness of 5.87 kgf and 6.20 kgf, The compositions of the tablets of Examples 21 to 28, and their test results for disintegration and hardness are shown in the following Table 6.

TABLE 6

(Unit of amount: g)

|     |     |     | Example 21 | Example 22 | Example 23 | Example 24 | Example 25 | Example 26 | Example 27 | Example 28 |
|---|---|---|---|---|---|---|---|---|---|---|
| (a) | Copolyvidone (Kollidon VA64) | | 12.0 | | 12.0 | | 12.0 | | 12.0 | |
| | Polyvinyl alcohol-polyethylene glycol graft copolymer (Kollicoat IR) | | | 12.0 | | 12.0 | | 12.0 | | 12.0 |
| (b) Additives | Tannic acid | | 6.0 | 6.0 | 6.0 | 6.0 | 6.0 | 6.0 | 6.0 | 6.0 |
| | Excipients | Mannitol | | | 510.6 | 510.6 | 510.6 | 510.6 | 510.6 | 510.6 |
| | | Lactose hydrate | 510.6 | 510.6 | | | | | | |
| | Binders | Magnesium aluminometasilicate | 9.0 | 9.0 | | | | | | |
| | | Synthetic aluminum silicate | | | 9.0 | 9.0 | | | | |
| | | Light silicic acid anhydride | | | | | 9.0 | 9.0 | | |
| | | Calcium silicate | | | | | | | 9.0 | 9.0 |
| | Crospovidone (disintegrant) | | 30.0 | 30.0 | 30.0 | 30.0 | 30.0 | 30.0 | 30.0 | 30.0 |
| | Aspartame (sweetener) | | 1.8 | 1.8 | 1.8 | 1.8 | 1.8 | 1.8 | 1.8 | 1.8 |
| | L-menthol (refrigerant) | | 0.6 | 0.6 | 0.6 | 0.6 | 0.6 | 0.6 | 0.6 | 0.6 |
| | Citric acid hydrate (corrigent) | | 3.0 | 3.0 | 3.0 | 3.0 | 3.0 | 3.0 | 3.0 | 3.0 |
| | Magnesium stearate (lubricant) | | 3.0 | 3.0 | 3.0 | 3.0 | 3.0 | 3.0 | 3.0 | 3.0 |
| Physical property values | Total amount (g) | | 576.0 | 576.0 | 576.0 | 576.0 | 576.0 | 576.0 | 576.0 | 576.0 |
| | Hardness (mean) (kgf) | | 5.37 | 5.36 | 5.86 | 6.20 | 5.87 | 7.26 | 5.38 | 6.18 |
| | Disintegration time (mean) (second) | | 12 | 21 | 12 | 16 | 9 | 18 | 10 | 14 |

As is clear from the test results in Table 6, the tablets of Examples 21 to 28 had a disintegration time of 9 to 21 seconds and a hardness of 5.36 to 7.26 kgf, and were excellent in disintegrability and moldability.

The compositions of the tablets of Examples 29 to 36 and Comparative Examples 19 to 26, and their test results for disintegration and hardness are shown in the following Tables 7 to 8.

TABLE 7

(Unit of amount: g)

|     |     | Example 29 | Example 30 | Example 31 | Example 32 | Example 33 | Example 34 | Example 35 | Example 36 |
|---|---|---|---|---|---|---|---|---|---|
| Pharmaceutically active ingredients | | Meclinize hydrochloride 30.0 | Scopolamine hydrobromide hydrate 0.3 | Famotidine 24.0 | | Ketotifen fumarate 3.312 | | Loperamide hydrochloride 1.2 | |
| (a) | Copolyvidone (Kollidon VA64) | 12.0 | | 12.0 | | 12.0 | | 12.0 | |
| | Polyvinyl alcohol-polyethylene glycol graft copolymer (Kollicoat IR) | | 12.0 | | 12.0 | | 12.0 | | 12.0 |
| (b) Additives | Tannic acid | 6.0 | 6.0 | 6.0 | 6.0 | 6.0 | 6.0 | 6.0 | 6.0 |
| | Mannitol (excipient) | 480.3 | 480.3 | 486.6 | 486.6 | 507.288 | 507.288 | 509.4 | 509.4 |
| | Magnesium aluminometasilicate (binder) | 9.0 | 9.0 | 9.0 | 9.0 | 9.0 | 9.0 | 9.0 | 9.0 |
| | Crospovidone (disintegrant) | 30.0 | 30.0 | 30.0 | 30.0 | 30.0 | 30.0 | 30.0 | 30.0 |
| | Aspartame (sweetener) | 1.8 | 1.8 | 1.8 | 1.8 | 1.8 | 1.8 | 1.8 | 1.8 |
| | L-menthol (refrigerant) | 0.6 | 0.6 | 0.6 | 0.6 | 0.6 | 0.6 | 0.6 | 0.6 |
| | Citric acid hydrate (corrigent) | 3.0 | 3.0 | 3.0 | 3.0 | 3.0 | 3.0 | 3.0 | 3.0 |
| | Magnesium stearate (lubricant) | 3.0 | 3.0 | 3.0 | 3.0 | 3.0 | 3.0 | 3.0 | 3.0 |
| Physical property values | Total amount (g) | 576.0 | 576.0 | 576.0 | 576.0 | 576.0 | 576.0 | 576.0 | 576.0 |
| | Hardness (mean) (kgf) | 6.24 | 7.35 | 7.11 | 7.07 | 6.23 | 7.07 | 7.00 | 7.42 |
| | Disintegration time (mean) (second) | 9 | 13 | 11 | 21 | 11 | 18 | 9 | 18 |

TABLE 8

(Unit of amount: g)

| | | Comparative Example 19 | Comparative Example 20 | Comparative Example 21 | Comparative Example 22 | Comparative Example 23 | Comparative Example 24 | Comparative Example 25 | Comparative Example 26 |
|---|---|---|---|---|---|---|---|---|---|
| Pharamaceutically active ingredients | | Meclizine hydrochloride 3.0 | Scopolamine hydrobromide hydrate 0.3 | Famotidine 24.0 | Famotidine 24.0 | Ketotifen fumarate 3.312 | Ketotifen fumarate 3.312 | Loperamide hydrochloride 1.2 | Loperamide hydrochloride 1.2 |
| (a) | Copolyvidone (Kollidon VA64) | 12.0 | | 12.0 | | 12.0 | | 12.0 | |
| | Polyvinyl alcohol-polyethylene glycol graft copolymer (Kollicoat IR) | | 12.0 | | 12.0 | | 12.0 | | 12.0 |
| (b) | Tannic acid | | | | | | | | |
| Additives | Mannitol (excipient) | 486.3 | 486.3 | 492.6 | 492.6 | 513.288 | 513.288 | 515.4 | 515.4 |
| | Magnesium aluminometasilicate (binder) | 9.0 | 9.0 | 9.0 | 9.0 | 9.0 | 9.0 | 9.0 | 9.0 |
| | Crospovidone (disintegrant) | 30.0 | 30.0 | 30.0 | 30.0 | 30.0 | 30.0 | 30.0 | 30.0 |
| | Aspartame (sweetener) | 1.8 | 1.8 | 1.8 | 1.8 | 1.8 | 1.8 | 1.8 | 1.8 |
| | L-menthol (refrigerant) | 0.6 | 0.6 | 0.6 | 0.6 | 0.6 | 0.6 | 0.6 | 0.6 |
| | Citric acid hydrate (corrigent) | 3.0 | 3.0 | 3.0 | 3.0 | 3.0 | 3.0 | 3.0 | 3.0 |
| | Magnesium stearate (lubricant) | 3.0 | 3.0 | 3.0 | 3.0 | 3.0 | 3.0 | 3.0 | 3.0 |
| Physical property values | Total amount (g) | 576.0 | 576.0 | 576.0 | 576.0 | 576.0 | 576.0 | 576.0 | 576.0 |
| | Hardness (mean) (kgf) | 6.59 | 7.28 | 7.11 | 7.39 | 6.91 | 7.10 | 7.03 | 7.08 |
| | Disintegration time (mean) (second) | 17 | 25 | 25 | 35 | 32 | 42 | 29 | 33 |

As is clear from the test results in Tables 7 to 8, the tablets of Examples 29 to 36 had a disintegration time of 9 to 21 seconds and a hardness of 6.23 to 7.42 kgf, and were excellent in disintegrability and moldability regardless of the kind of the pharmaceutically active ingredient used. In contrast, the tablets of Comparative Examples 19 to 26, which did not contain the ingredient (b), had a disintegration time of 17 to 42 seconds, and were inferior in disintegrability to the tablets of Examples 29 to 36.

INDUSTRIAL APPLICABILITY

The orally fast disintegrating tablet of the present invention can be produced without the use of any complicated production process or any special production equipment, and is excellent in both disintegrability and moldability regardless of the kind of the pharmaceutically active ingredient contained in the tablet. Therefore, the tablet of the present invention can be widely used as an orally fast disintegrating tablet that is suitable for industrial mass production and can contain a variety of pharmaceutically active ingredients.

The invention claimed is:

1. An orally fast disintegrating tablet containing a granular material which comprises (a) at least one kind of water soluble polymer and (b) tannic acid.

2. The orally fast disintegrating tablet according to claim 1, further containing a binder and/or a disintegrant.

3. The orally fast disintegrating tablet according to claim 2, wherein the binder is at least one kind selected from the group consisting of magnesium aluminometasilicate, synthetic aluminum silicate, light silicic acid anhydride, calcium silicate and crystalline cellulose.

4. The orally fast disintegrating tablet according to claim 2, wherein the disintegrant is at least one kind selected from the group consisting of crospovidone, carmellose, carmellose calcium, croscarmellose sodium and low-substituted hydroxypropyl cellulose.

5. The orally fast disintegrating tablet according to claim 1, having a disintegration time of 30 seconds or less as measured by a disintegration test specified in the Japanese Pharmacopoeia.

6. The orally fast disintegrating tablet according to claim 1, having a hardness of 5 kgf to 7.42 kgf.

7. A method for producing an orally fast disintegrating tablet, comprising compression molding of
(A) a granular material which comprises (a) at least one kind of water soluble polymer and (b) tannic acid, or
(B) a mixture of a granular material which comprises (a) at least one kind of water soluble polymer and (b) tannic acid, and an additive and/or a pharmaceutically active ingredient.

8. The method according to claim 7, wherein the additive is a binder and/or a disintegrant.

9. The orally fast disintegrating tablet according to claim 1, wherein the at least one kind of water soluble polymer is selected from the group consisting of povidone, hydroxypropyl cellulose, pullulan, a polyvinyl alcohol-polyethylene glycol graft copolymer and copolyvidone.

10. The granular material for orally fast disintegrating tablets according to claim 1, wherein the content of the ingredient (a) is 0.001 to 60% by weight relative to the total weight of the granular material.

11. The granular material for orally fast disintegrating tablets according to claim 1, wherein the content of the ingredient (b) is 0.001 to 60% by weight relative to the total weight of the granular material.

12. The granular material for orally fast disintegrating tablets according to claim 1, further comprising an excipient.

13. The granular material for orally fast disintegrating tablets according to claim 12, wherein the excipient is at least one kind selected from the group consisting of mannitol and lactose hydrate.

14. The method according to claim 7, wherein the at least one kind of water soluble polymer is selected from the group consisting of povidone, hydroxypropyl cellulose, pullulan, a polyvinyl alcohol-polyethylene glycol graft copolymer and copolyvidone.

15. The method according to claim 7, wherein the content of the ingredient (a) is 0.001 to 60% by weight relative to the total weight of the granular material.

16. The method according to claim 7, wherein the content of the ingredient (b) is 0.001 to 60% by weight relative to the total weight of the granular material.

17. The method according to claim 7, further comprising an excipient.

18. The method according to claim 17, wherein the excipient is at least one kind selected from the group consisting of mannitol and lactose hydrate.

* * * * *